United States Patent [19]

Ammermann et al.

[11] 4,359,471
[45] Nov. 16, 1982

[54] 2-(N-ARYL,N-1,2,3-THIADIAZOLYLCAR-BONYL)-AMINOBUTYRO-LACTONES, THEIR PREPARATION, FUNGICIDAL AGENTS CONTAINING THESE COMPOUNDS, AND THEIR USE AS FUNGICIDES

[75] Inventors: Eberhard Ammermann; Bernd Zeeh, both of Ludwigshafen; Gerhard Hamprecht, Weinheim; Ernst-Heinrich Pommer, Limburgerhof, all of Fed. Rep. of Germany

[73] Assignee: BASF Aktiengesellschaft, Fed. Rep. of Germany

[21] Appl. No.: 312,314

[22] Filed: Oct. 16, 1981

[30] Foreign Application Priority Data

Nov. 8, 1980 [DE] Fed. Rep. of Germany ....... 3042195

[51] Int. Cl.³ .................. C07D 417/12; A01N 43/82
[52] U.S. Cl. .................... 424/269; 548/127; 71/92
[58] Field of Search .................. 548/127; 424/269

[56] References Cited
U.S. PATENT DOCUMENTS 3,933,860  1/1976  Chan ................. 260/343.5
4,147,792  4/1979  Kunz et al. ............ 424/269
4,177,054  12/1979  Arndt et al. ........... 548/127

FOREIGN PATENT DOCUMENTS 2804299  11/1977  Fed. Rep. of Germany.

*Primary Examiner*—Mary C. Lee
*Attorney, Agent, or Firm*—Keil & Witherspoon

[57] ABSTRACT

2-(N-Aryl,N-1,2,3-thiadiazolylcarbonyl)-aminobutyrolactones of the formula

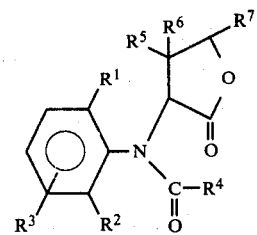

where $R^1$ is alkyl, $R^2$ is hydrogen, alkyl or halogen, $R^3$ is hydrogen, alkyl or halogen, $R^4$ is unsubstituted or substituted 1,2,3-thiadiazolyl and $R^5$, $R^6$ and $R^7$, independently of one another, are hydrogen or methyl, and fungicides containing these compounds.

3 Claims, No Drawings

2-(N-ARYL,N-1,2,3-THIADIAZOLYLCARBONYL)-AMINOBUTYRO-LACTONES, THEIR PREPARATION, FUNGICIDAL AGENTS CONTAINING THESE COMPOUNDS, AND THEIR USE AS FUNGICIDES

The present invention relates to novel 2-(N-aryl,N-1,2,3-thiadiazolylcarbonyl)-aminobutyrolactones, to a process for their preparation, to fungicides which contain these compounds as active ingredients, and to methods of controlling harmful fungi with these active ingredients.

2-(N-aryl,N-arylcarbonyl)-aminobutyrolactones which act as fungicides, for example 2-(N-2,6-dimethylphenyl,N-3,4-dichlorophenylcarbonyl)-aminobutyrolactone, are known from U.S. Pat. No. 3,933,860 (cf. Example 2 therein). However, the above compound is insufficiently effective against lower fungi, such as Phytophthora. Further, the use of N-trichloromethylthiotetrahydrophthalimide as a fungicide is known from Chemical Week, June 21, 1972, page 46. However, its fungicidal action is inadequate.

We have found that 2-(N-aryl,N-1,2,3-thiadiazolylcarbonyl)-aminobutyrolactones of the general formula I

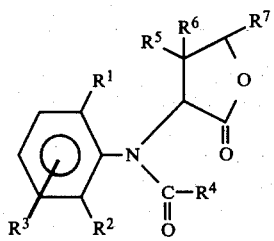

where $R^1$ is $C_1$–$C_3$-alkyl (preferably methyl or ethyl), $R^2$ is hydrogen, $C_1$–$C_3$-alkyl (preferably methyl or ethyl) or halogen (preferably chlorine or bromine), $R^3$ is hydrogen, $C_1$–$C_3$-alkyl (preferably methyl or ethyl) or halogen (preferably chlorine or bromine), $R^4$ is unsubstituted or halogen-substituted (preferably chlorine-substituted or bromine-substituted) 1,2,3-thiadiazol-4-yl or -5-yl and $R^5$, $R^6$ and $R^7$ independently of one another are hydrogen or methyl, have an excellent fungicidal action and are more effective, especially against Phytophthora, than the conventional 2-(N-aryl,N-arylcarbonyl)-aminobutyrolactones.

The 2-(N-aryl,N-1,2,3-thiadiazolylcarbonyl)-aminobutyrolactones of the formula I have centers of asymmetry in carbon atom 2, and may or may not also have such centers in carbon atoms 3 and 4, of the butyrolactone ring. Accordingly, they form enantiomers.

The optically pure enantiomers can be obtained by conventional methods. Both the mixtures usually obtained from the synthesis, and the pure enantiomers, have a fungicidal action. Accordingly, the invention encompasses the pure enantiomers as well as their mixtures.

The 2-(N-aryl,N-1,2,3-thiadiazolylcarbonyl)-aminobutyrolactones of the formula I can be obtained by reacting a 2-(N-aryl)-aminobutyrolactone of the formula II

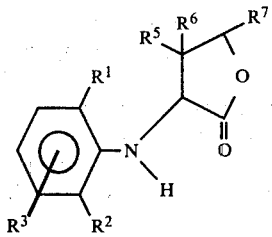

where $R^1$, $R^2$, $R^3$, $R^5$, $R^6$ and $R^7$ have the above meanings, with a carboxylic acid derivative of the formula III

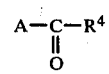

where $R^4$ has the above meanings and A is a nucleophilically displaceable leaving group, in the presence or absence of a solvent or diluent, in the presence or absence of an inorganic or organic base, and in the presence or absence of a reaction accelerator, at from 0° to 120° C.

In formula III, A is, for example, halogen, eg. chlorine or bromine, alkoxycarbonyloxy, eg. methoxycarbonyloxy or ethoxycarbonyloxy, benzoxycarbonyloxy or azolyl, eg. imidazolyl or triazolyl.

The reaction can be carried out in the presence of a solvent or diluent. The preferred solvents or diluents include halohydrocarbons, eg. methylene chloride, chloroform, 1,2-dichloroethane and chlorobenzene, aliphatic or aromatic hydrocarbons, eg. cyclohexane, petroleum ether, benzene, toluene and xylenes, esters, eg. ethyl acetate, nitriles, eg. acetonitrile, sulfoxides, eg. dimethyl sulfoxide, ketones, eg. acetone and methyl ethyl ketone, ethers, eg. diethyl ether, tetrahydrofuran and dioxane, and mixtures of these liquids.

Advantageously, the solvent or diluent is used in an amount of from 100 to 2,000% by weight, preferably from 100 to 1,000% by weight, based on the starting material of the formula II.

Examples of suitable inorganic or organic bases which may be added to the reaction mixture as acid acceptors are alkali metal carbonates, eg. potassium carbonate and sodium carbonate, alkali metal hydrides, eg. sodium hydride, tertiary amines, eg. trimethylamine, triethylamine, N,N-dimethylaniline, N,N-dimethylcyclohexylamine, N-methylpiperidine and pyridine, and azoles, eg. 1,2,4-triazole and imidazole. However, other conventional bases may also be used.

Preferred reaction accelerators are metal halides, eg. sodium bromide or potassium iodide, azoles, eg. imidazole or 1,2,4-triazole or pyridines, eg. 4-dimethylaminopyridine, or mixtures of these substances. Advantageously, from 0.9 to 1.3 moles of the acid derivative of the formula III, with or without from 0.5 to 2 moles of base, and with or without from 0.01 to 0.1 mole of reaction accelerator, are employed per mole of aniline derivative of the formula II.

The reaction is in general carried out at from 0° to 120° C., for a period of from 1 to 60 hours, under atmospheric or superatmospheric pressure, continuously or batchwise.

In a preferred embodiment of the process according to the invention, the starting material of the formula II is mixed with a base, if used, and a diluent, if used, the acid derivative of the formula III and the reaction accelerator, if used, are then added and the reaction mixture is kept at the reaction temperature, which can be from 0° to 120° C., for from 0.5 to 12 hours, preferably from 1 to 6 hours.

The novel compounds may be isolated by, for example, removing any diluent present, then dissolving the residue in an organic solvent, and washing the solution with a dilute acid and then with aqueous dilute caustic alkali and with water in order to remove the excess base and the starting materials II and III.

The products which remain after the solvent is distilled off do not in general require further purification, but if such purification is needed it can be effected by conventional methods, for example by recrystallization, extraction or chromatography.

The anilines of the formula II are known (German Laid-Open Application DOS No. 2,845,454) or can be prepared by conventional methods.

The carboxylic acid derivatives of the formula III, used as starting materials, are also known or can be prepared by conventional methods, as described in J.Amer. Chem.Soc. 77 (1955), 5359, and J. Chem. Soc. 1965, 5166.

The Example which follows illustrates the preparation of the 2-(N-aryl,N-1,2,3-thiadiazolylcarbonyl)aminobutyrolactones of the formula I.

EXAMPLE 1

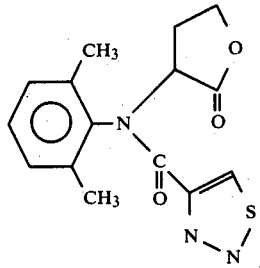

A solution of 14.8 g of 1,2,3-thiadiazol-4-carboxylic acid chloride in 50 ml of methylene chloride is added dropwise to a stirred suspension of 20.5 g of 2-(N-2,6-dimethylphenyl)-aminobutyrolactone, 20.7 g of potassium carbonate and 0.1 g of 4-dimethylaminopyridine in 200 ml of methylene chloride, and the mixture is stirred overnight at room temperature. After the inorganic salts have been separated off, the organic phase is washed three times with water, dried and evaporated down. Recrystallization of the residue from diethyl ether gives 22 g of 2-(N-2,6-dimethylphenyl,N-1,2,3-thiadiazol-4-ylcarbonyl)aminobutyrolactone, of melting point 169°–174° C.

The following are examples of compounds of the formula I which can be prepared by a similar method:

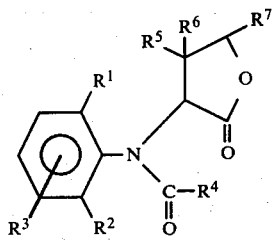

TABLE 1

| No. | $R^1$ | $R^2$ | $R^3$ | $R^4$ | $R^5$ | $R^6$ | $R^7$ | m.p. (°C.) |
|---|---|---|---|---|---|---|---|---|
| 2 | $CH_3$ | Cl | H | 1,2,3-Thiadiazol-4-yl | H | H | H | 162–170 |
| 3 | $CH_3$ | $CH_3$ | H | 1,2,3-Thiadiazol-4-yl | H | H | $CH_3$ | 126–128 |
| 4 | $CH_3$ | $CH_3$ | 3-$CH_3$ | 1,2,3-Thiadiazol-4-yl | H | H | H | 152–155 |
| 5 | $CH_3$ | $C_2H_5$ | H | 1,2,3-Thiadiazol-4-yl | H | H | H | 124–127 |
| 6 | $CH_3$ | H | H | 1,2,3-Thiadiazol-4-yl | H | H | H | 143 |
| 7 | $CH_3$ | $CH_3$ | H | 1,2,3-Thiadiazol-5-yl | H | H | H | 206–208 |
| 8 | $CH_3$ | Cl | H | 1,2,3-Thiadiazol-5-yl | H | H | H | |
| 9 | $C_2H_5$ | $CH_3$ | H | 1,2,3-Thiadiazol-5-yl | H | H | H | |
| 10 | $CH_3$ | $CH_3$ | H | 5-Chloro-1,2,3-thiadiazol-4-yl | H | H | H | |
| 11 | $CH_3$ | $C_2H_5$ | H | 5-Chloro-1,2,3-thiadiazol-4-yl | H | H | H | |
| 12 | $CH_3$ | H | H | 5-Chloro-1,2,3-thiadiazol-4-yl | $CH_3$ | $CH_3$ | H | |

The active ingredients according to the invention have a strong fungitoxic action. They are suitable for combating phytopathogenic fungi. They cause no damage to crop plants in the concentrations necessary for combating fungi and bacteria. For these reasons they are suitable for use as crop protection agents for fighting fungi.

They are suitable for combating for instance *Phytophthora cactorum* in apples, *Phytophthora infestans* in tomatoes and potatoes, *Phytophthora parasitica* in strawberries, *Pseudoperonospora cubensis* in cucumbers, *Pseudoperonospora humuli* in hops, *Peronospora destructor* in onions, *Peronospora viticola* in grapes, *Plasmopara halstedii* in sunflowers, *Sclerospora macrospora* in Indian corn, and *Bremia lactucae* in lettuce.

The application rates depend on the type of effect desired, and range from 0.025 to 5 kg of active ingredient per hectare. Some of the active ingredients have curative properties, i.e., the agents may also be applied after the plants have been infected by the pathogen, and success is still ensured. Furthermore, many of the new compounds have a systemic action, which means that visible plant parts may also be protected by a root treatment.

The new compounds may also be employed to control fungi which cause seedling and emergence diseases, e.g., Pythium and Aphanomyces species in Leguminosae and cotton. The agents are applied as seed disinfectants at rates of from 10 to 200 g per 100 kg of seed.

The compounds are applied by spraying or dusting the plants with the active ingredients, or treating the seed with them. The compounds may be applied before or after infection of the plants or seed by the fungi.

The active ingredients of the invention can be converted into the conventional formulations, e.g. solutions, emulsions, suspensions, dusts, powders, pastes and granules. The form of application depends entirely on the purpose for which the agent is to be used; at all events, it should ensure as fine and uniform a distribution of the active ingredients as possible. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.g. petroleum fractions, alcohols, e.g. methanol and butanol, amines, e.g. ethanolamine, and dimethylformamide and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The fungicidal agents generally contain from 0.1 to 95, preferably from 0.5 to 90, wt% of active ingredient.

The agents and the ready-to-use formulations obtained therefrom, e.g., solutions, emulsions, suspensions, powders, dusts, pastes or granules, are applied in the conventional manner, e.g. by spraying, atomizing, dusting, scattering, treating seed, or watering.

Examples of such formulations are given below:

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 1 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil. By pouring the solution into water and uniformly distributing it therein, an aqueous dispersion is obtained.

III. 20 parts by weight of compound no. 5 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into water and finely distributing it therein, an aqueous dispersion is obtained.

IV. 20 parts by weight of compound no. 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into water and uniformly distributing it therein, an aqueous dispersion is obtained.

V. 80 parts by weight of compound no. 5 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 3 is intimately mixed with 97 parts by weight of particulate kaolin. A dust is obtained containing 3% by weight of the active ingredient.

VII. 30 parts by weight of compound no. 4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 2 is intimately mixed with 10 parts of the sodium salt of a phenolsulfonic acid-urea-formaldehyde condensate, 2 parts of silica gel and 48 parts of water to give a stable, aqueous dispersion. Dilution in water gives an aqueous dispersion.

IX. 20 parts of compound no. 4 is intimately mixed with 2 parts of the calcium salt of dodecylbenzenesulfonic acid, 8 parts of a fatty alcohol polyglycol ether, 2 parts of the sodium salt of a phenolsulfonic acid-ureaformaldehyde condensate and 68 parts of a paraffinic mineral oil. A stable oily dispersion is obtained.

The above ready-to-use preparations may contain other active ingredients together with those according to the invention, e.g. herbicides, insecticides, growth regulators and other fungicides or may be mixed with fertilizers and applied together with these. When the active ingredients are mixed with other fungicides, the fungicidal spectrum of action is in many cases broadened.

The list of fungicides given below, with which the compounds according to the invention can be combined, is intended to illustrate the possible combinations, but the invention is in no way limited to these.

Examples of fungicides which can be combined with the compounds of the invention are: dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and zinc N,N'-propylene-bis-dithiocarbamate, and the ammonia complex of zinc N,N'-propylene-bis-dithiocarbamate and N,N'-polypropylene-bis-(thiocarbamoyl)-disulfide; nitro derivatives, e.g. dinitro-(1-methylheptyl)-phenyl crotonate, 2-sec.-butyl-4,6-dinitrophenyl-3,3-dimethylacrylate and 2-sec.-butyl-4,6-dinitrophenyl isopropyl carbonate; heterocyclic compounds, e.g. N-trichloromethylthiotetrahydrophthalimide, N-(1,1,2,2-tetrachloroethylthio)-tetrahydrophthalimide, N-trichloromethylthio-phthalimide, 2-heptadecyl-2-imidazoline acetate, 2,4-dichloro-6-(o-chloroanilino)-s-triazine, 0,0-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenylhydrazono)-3-methyl-5-isoxazolone, pyridine-2-thio-1-oxide, 8-hydroxyquinoline and its copper salt, 2,3-dihydro-5-carboxanilido-6-methyl-1,4-oxathiine-4,4-dioxide, 2,3-dihydro-5-carboxanilido-6-methyl-1,4-oxathine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6- methylpyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thiouredio)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2,5-dimethylfuran-3-carboxylic acid cyclohexylamide, 2-methyl-benzoic acid anilide, 2-iodobenzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclodecyl-morpholine and its salts, diisopropyl 5-nitroisophthalate, 1-(1',2',4'-triazol-1'-yl)-(4'-chlorophenoxy)-3,3-dimethylbutan-2-one, 1-(1',2',4'-triazol-1'-yl)-(4'-chlorophenoxy)-3,3-dimethylbutan-2-ol, N-(n-propyl)-N-(2,4,6-trichlorophenoxyethyl)-N'-imidazolylurea, N-cyclohexyl-N-methoxy-2,5-dimethylfuran-3-carboxylic acid amide, 2,4,5-trimethylfuran-3-carboxylic acid anilide, 5-methyl-5-vinyl-3-(3,5-dichlorophenyl)-2,4-dioxo-1,3-oxazolidine, 5-methoxymethyl-5-methyl-3-(3,5-dichlorophenyl)-2,4-dioxo-1,3-oxazolidine, and N-[3-(p-tert-butylphenyl)-2-methylpropyl]-cis-2,6-dimethyl-morpholine.

The following experiments illustrate the fungicidal action of the novel compounds.

The prior art compound N-trichloromethylthiotetrahydrophthalimide (A) and 2-(N-2,6-dimethylphenyl-N-3,4-dichlorophenylcarbonyl)-aminobutyrolactone (B) disclosed in Example 2 of U.S. Pat. No. 3,933,860 were employed as comparative agents.

EXAMPLE 1

Fungicidal action on *Phytophthora infestans* in tomatoes

Leaves of tomato plants of the "Professor Rudloff" variety are sprayed with aqueous suspensions containing (dry basis) 80% (wt%) of active ingredient and 20% of sodium lignin sulfonate. 0.025 and 0.006% (dry basis) spray liquors are used. After the sprayed-on layer has dried, the leaves are infected with a zoospore suspension of Phytophthora infestans. The plants are then placed for 5 days in a steam-saturated (moist) chamber kept at 16° to 18° C. After this period, the disease has spread on the untreated control plants to such an extent that the fungicidal action of the compounds can be assessed.

In this experiment, active ingredients nos. 1, 2, 3 and 4 had a better fungicidal action than prior art active ingredient B.

EXAMPLE 2

Fungicidal action on *Plasmopara viticola* in grapes

Leaves of potted vines of the Müller-Thurgau variety are sprayed with aqueous emulsions containing (dry basis) 80% (by weight) of the active ingredient and 20% of emulsifier. 0.025 and 0.006% spray liquors (dry basis) are used. The leaves are then infected with a zoospore suspension of Plasmopara viticola. The plants are then placed for 16 hours in a steam-saturated (moist) chamber of 20° C., and subsequently for 8 days in the greenhouse at 20° C. to 30° C. To accelerate and intensify the sporangiophore discharge, the plants are then again placed in the moist chamber for 16 hours. The extent of fungus spread is assessed on the undersides of the leaves. Untreated, infected control plants are used for comparison.

In this experiment, active ingredients nos. 2, 3, 4 and 5 have a good fungicidal action.

EXAMPLE 3

Fungicidal action on emergence diseases in peas 100 g samples of pea seeds of the "Senator" variety are carefully shaken for about 5 minutes in glass bottles with 300 mg (=0.3 wt%) of seed disinfectant formulations containing (dry basis) 40% of active ingredient. Subsequently, 100 seeds are sown 3 cm deep and 3 to 5 cm apart in pots in a compost naturally and heavily infested with the fungi Pythium spec., Aphanomyces spec. and Fusarium oxysporum. The boxes are set up in the greenhouse at from 17° to 20° C. The number of healthy pea plants is determined after 21 days.

The results show that new active ingredients 1 and 2 have better fungicidal action than prior art comparative agents A and B. After treatment with active ingredients 1 and 2, there were almost as many healthy pea plants as in sterilized compost.

We claim:

1. A 2-(N-aryl,N-1,2,3-thiadiazolylcarbonyl)-aminobutyrolactone of the formula

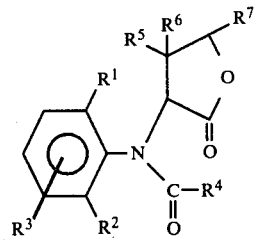

where $R^1$ is $C_1$–$C_3$-alkyl, $R^2$ is hydrogen, $C_1$–$C_3$-alkyl or halogen, $R^3$ is hydrogen, $C_1$–$C_3$-alkyl or halogen, $R^4$ is unsubstituted or halogen-substituted 1,2,3-thiadiazol-4-yl or -5-yl and $R^5$, $R^6$ and $R^7$, independently of one another, are hydrogen or methyl.

2. A process for combating fungi, wherein the fungi or the objects to be protected against fungus attack are treated with a 2-(N-aryl,N-1,2,3-thiadiazolylcarbonyl)-aminobutyrolactone of the formula

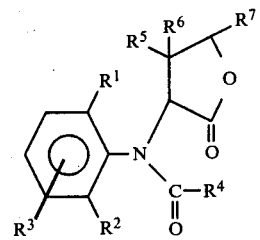

where $R^1$ is $C_1$–$C_3$-alkyl, $R^2$ is hydrogen, $C_1$–$C_3$-alkyl or halogen, $R^3$ is hydrogen, $C_1$–$C_3$-alkyl or halogen, $R^4$ is unsubstituted or halogen-substituted 1,2,3-thiadiazol-4-yl or -5-yl and $R^5$, $R^6$ and $R^7$, independently of one another, are hydrogen or methyl.

3. A 2-(N-aryl,N-1,2,3-thiadiazolylcarbonyl)-aminobutyrolactone selected from the group consisting of 2-(N-2,6-dimethylphenyl,N-1,2,3-thiadiazol-4-ylcarbonyl)-aminobutyrolactone and 2-(N-2-methyl-6-chlorophenyl,N-1,2,3-thiadiazol-4-ylcarbonyl)-aminobutyrolactone.

* * * * *